US010772558B2

(12) United States Patent
Breuille et al.

(10) Patent No.: US 10,772,558 B2
(45) Date of Patent: Sep. 15, 2020

(54) ASSESSMENT AND ADVICE ON NUTRITION, ENDURANCE, AND STRENGTH

(71) Applicant: NESTEC S.A., Vevey (CH)

(72) Inventors: Denis Breuille, Lausanne (CH); Elizabeth Offord Cavin, Montreux (CH); Daniel Ryan Moore, Ontario (CA); Richard Gannon, Lausanne (CH); Marie Noelle Horcajada, Echenevex (FR); Aline Boisset Michaud, Chardonne (CH); Michaela Hoehne, Vevey (CH)

(73) Assignee: Societe des Produits Nestle S.A., Vevey (CH)

( * ) Notice: Subject to any disclaimer, the term of this patent is extended or adjusted under 35 U.S.C. 154(b) by 345 days.

(21) Appl. No.: 14/766,518

(22) PCT Filed: Jan. 24, 2014

(86) PCT No.: PCT/EP2014/051381
§ 371 (c)(1),
(2) Date: Aug. 7, 2015

(87) PCT Pub. No.: WO2014/122032
PCT Pub. Date: Aug. 14, 2014

(65) Prior Publication Data
US 2015/0374281 A1  Dec. 31, 2015

Related U.S. Application Data

(60) Provisional application No. 61/762,697, filed on Feb. 8, 2013.

(30) Foreign Application Priority Data

Feb. 8, 2013 (EP) .................................... 13154530

(51) Int. Cl.
*A61B 5/00* (2006.01)
*A61B 5/22* (2006.01)
(Continued)

(52) U.S. Cl.
CPC .............. *A61B 5/486* (2013.01); *A61B 5/112* (2013.01); *A61B 5/225* (2013.01); *A61B 5/4866* (2013.01);
(Continued)

(58) Field of Classification Search
None
See application file for complete search history.

(56) References Cited

U.S. PATENT DOCUMENTS 5,412,560 A    5/1995  Dennison
8,762,101 B2*  6/2014  Yuen ................... A61B 5/6838
                                                        702/160

(Continued)

FOREIGN PATENT DOCUMENTS

CN        1723838 A     1/2006
CN      201572084 U     9/2010
(Continued)

OTHER PUBLICATIONS

Internet Archive MNA Website Screencap Dec. 30, 2011 | Internet Archive WayBack Machine URL: https://web.archive.org/web/20111230040757/https://www.mna-elderly.com/.*
(Continued)

*Primary Examiner* — Sean P Dougherty
*Assistant Examiner* — Benjamin S Melhus
(74) *Attorney, Agent, or Firm* — K&L Gates LLP

(57) ABSTRACT

The present invention relates to a new integrated, holistic approach to empower older adults to enhance their quality of life and independence through a personalized lifestyle and nutrition program. This is achieved by measuring the physi-
(Continued)

cal status of the adults with respect to strength and endurance. In addition, their nutritional status is assessed. Based on those assessments recommendations are provided with respect to particular exercise programs and nutrients that support the functions bones, muscles and cartilage. These methods can be implemented as a software program and executed on computer systems.

13 Claims, 4 Drawing Sheets

(51) Int. Cl.
    *A61B 5/11*     (2006.01)
    *G06F 19/00*     (2018.01)
    *G06Q 50/22*     (2018.01)

(52) U.S. Cl.
    CPC .......... *A61B 5/4884* (2013.01); *A61B 5/7264* (2013.01); *G06F 19/3475* (2013.01); *G06F 19/3481* (2013.01); *G06Q 50/22* (2013.01); *A61B 2503/08* (2013.01); *A61B 2560/0475* (2013.01)

(56) References Cited

U.S. PATENT DOCUMENTS

| | | | |
|---|---|---|---|
| 8,935,123 B2* | 1/2015 | Yuen | A61B 5/6838 |
| | | | 702/160 |
| 9,081,534 B2* | 7/2015 | Yuen | G06F 11/00 |
| 2003/0088197 A1* | 5/2003 | Itagaki | A61B 5/0537 |
| | | | 600/595 |
| 2008/0086318 A1 | 4/2008 | Gilley et al. | |
| 2008/0132383 A1* | 6/2008 | Einav | A61H 1/02 |
| | | | 482/8 |
| 2010/0049095 A1* | 2/2010 | Bunn | A61B 5/1038 |
| | | | 600/595 |
| 2011/0004126 A1* | 1/2011 | Einav | G06F 19/3481 |
| | | | 600/595 |
| 2012/0040799 A1* | 2/2012 | Jaquish | A63B 21/00047 |
| | | | 482/9 |
| 2012/0059230 A1 | 3/2012 | Teller et al. | |
| 2012/0083669 A1 | 4/2012 | Abujbara | |
| 2012/0196256 A1* | 8/2012 | Maeueler | A63B 24/0075 |
| | | | 434/247 |
| 2013/0158368 A1* | 6/2013 | Pacione | A61B 5/0022 |
| | | | 600/301 |
| 2013/0281888 A1* | 10/2013 | Bender | A61B 5/1116 |
| | | | 600/595 |
| 2013/0337974 A1* | 12/2013 | Yanev | G06F 19/3481 |
| | | | 482/8 |
| 2014/0088444 A1* | 3/2014 | Saalasti | A61B 5/0205 |
| | | | 600/484 |

FOREIGN PATENT DOCUMENTS

| | | |
|---|---|---|
| CN | 102549590 A | 7/2012 |
| CN | 102902881 A | 1/2013 |
| JP | 2002024405 | 1/2002 |
| JP | 2004054591 | 2/2004 |
| JP | 2004252604 A | 9/2004 |
| JP | 2006031433 | 2/2006 |
| JP | 2006260082 | 9/2006 |
| JP | 2008026950 A | 2/2008 |
| JP | 2009244964 | 10/2009 |
| KR | 20110050954 A | 5/2011 |
| WO | 2011080603 | 7/2011 |

OTHER PUBLICATIONS

EPO "Notice from the European Patent Office dated Oct. 1, 2007 concerning business methods" Official Journal of the European Patent Office, OEB, Munich, Germany, vol. 30, No. 11, Nov. 1, 2007, pp. 592-593, XP007905525.

Japanese Patent Office Communication for related application No. 2015-556446, Dispatch No. 031693, Dispatch Date Jan. 30, 2018, 11 pages.

\* cited by examiner

ASSESSMENT AND ADVICE ON NUTRITION, ENDURANCE, AND STRENGTH

CROSS REFERENCE TO RELATED APPLICATIONS

The present application is a National Stage of International Application No. PCT/EP2014/051381, filed on Jan. 24, 2014, which claims priority to European Patent Application No. 13154530.3, filed on Feb. 8, 2013, and U.S. Provisional Application Ser. No. 61/762,697, filed on Feb. 8, 2013, the entire contents of which are being incorporated herein by reference.

BACKGROUND

For the past decades the Western world and Japan observe a rise of the number of the elderly in the population. It is often observed that those elderly become frail and dependent on assistance. However, the development of frailty does not need to be inevitable. Appropriate advice and training of older adults can prevent many negative developments. It is therefore desirable to assist the elderly in maintaining or achieving an acceptable health status for a better quality of life. Previous approaches to the problem have generally involved providing unpersonalized, general recommendations to specific populations without fair consideration for potentially important differences between individuals in regards to their nutritional intake and physical capabilities. It is more likely that a personalized approach with exercise and specific nutrient would be more efficient in enhancing musculoskeletal health. Such personalized recommendations are possible at the only condition of having done a personalized evaluation of both the nutritional state and the physical ability/condition of the subject. Therefore, a novel approach is required for being able to perform such an evaluation in a short period of time. This approach should provide a coordinated method for providing advice and training to older adults.

SUMMARY

The invention relates to a computer-implemented method for determining the physical status of a subject comprising: providing a classification system for the parameters nutrition, physical endurance, and physical strength of said subject; assessing and scoring values of said parameters in said subject; using the obtained scores to classify the subject into classes with respect to each of said parameters; and using said determined classes for each parameter to determine the physical status of said subject.

In the first step of said method it can be determined whether the subject is suitable for being subjected to the method of the invention. The subject can be an older subject, preferentially a human subject being older than 65 years. The parameter endurance can be assessed by having a subject walk for a predetermined time or over a certain distance. The parameter strength can be assessed by measuring the strength of a hand grip or by performing a Sit-to-Stand test. The parameter nutrition can be assessed by the MNA and/or the evaluation of daily protein intake. The steps of the method can be performed with within 30 or 90 minutes. The steps can be repeated in defined intervals, preferentially every 8-16 weeks.

In a further embodiment the invention relates to a computer-implemented method for improving the physical status of a subject comprising: determining the physical status of a subject according to any of the above described methods; providing recommendations for the subject with respect to nutrition, physical endurance, and physical strength based on the determined scores wherein the nutrition contains bioactive nutrients improving physical endurance and physical strength.

Based on the determined class for the parameter physical endurance a particular exercise program can be recommended, wherein the exercise program is different for each determined class. Based on the determined class for the parameter physical strength a particular exercise program can be recommended, wherein the exercise program is different for each determined class.

In a further embodiment a system for determining the physical status of a subject, said system comprising a computer: said computer stores a data based comprising a classification system for the parameters nutrition, physical endurance, and physical strength of a subject; said computer stores a software program having instructions causing the computer to receive and store the values of said parameters in said subject; to score values of said parameters in said subject, to use the obtained scores to classify the subject into classes with respect to each of said parameters, and to output said class and thereby indicating the physical status of said subject based on said classes.

In a further embodiment the invention relates to a system for facilitating the improvement of a physical status of a subject, said system comprising a computer: said computer stores a data based comprising a classification system for the parameters nutrition, physical endurance, and physical strength of a subject; said computer stores a software program having instructions causing the computer to receive and store the values of said parameters in said subject, to score values of said parameters in said subject, to use the obtained scores to classify the subject into classes with respect to each of said parameters, relating recommendations for the subject with respect to nutrition, physical endurance, and physical strength based on the determined classes, and outputting said recommendations.

In a further embodiment the invention relates to a method for personalizing elderly care comprising the steps of: creating a database relating to physical functional tests and their validity to identifying the overall physical status of select elderly patient populations; storing the database on a computer; executing a computer program causing the computer to determine viable functional test results relating to strength and endurance and to the nutritional status in specific elderly patient populations, the test results including end points relating to nutrition, strength and endurance; and executing a program that uses the end points to generate guidelines based on nutrition, strength and endurance test results that can be used to personalize a nutrition and exercise program for a member of the specific elderly population.

At least two or three different programs can be used by the computer. The computer program can be executed by the computer to personalize the nutrition and exercise program for the member. The computer program can also contain a step relating the physical status to recommendations for the member and outputting those recommendations. During the program the member can be monitored to determine nutrition, strength and endurance. Depending on the results of the monitoring the nutrition and exercise program can be modified. The exercise programs can be endurance and strength exercise programs adapted to the particular needs of the member.

DEFINITIONS

Figure 1:
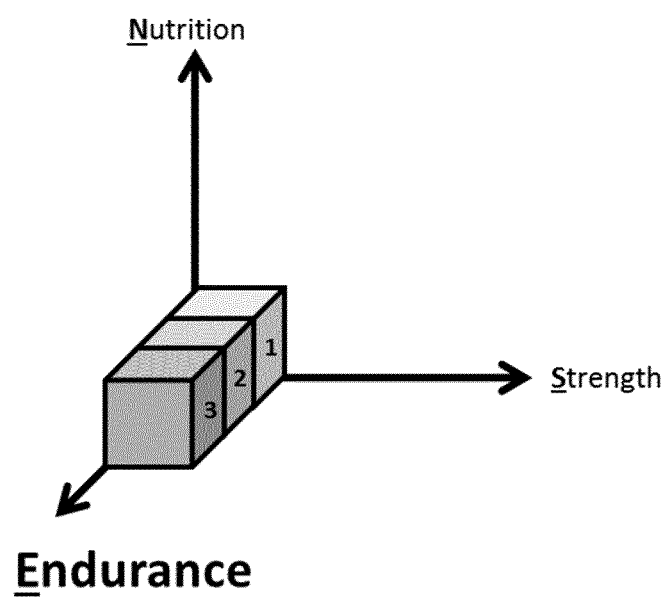
FIG. 1 schematically shows how a person within the three-parameter scheme can be assessed with respect to a classification in level 1, 2 or 3 for each of the parameter evaluated: nutrition, endurance, and strength.
Figure 2:
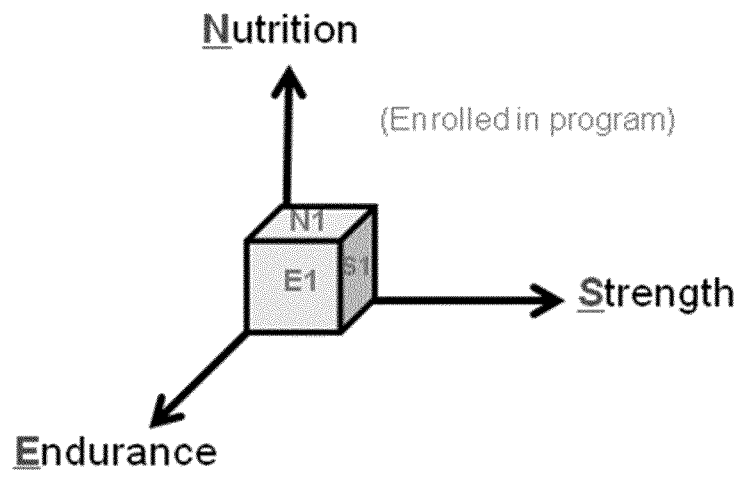
FIG. 2 schematically shows which parameters (Nutrition, Strength, Endurance) are to be determined with the method of the inventions. Their status is first determined (top part of figure) and after appropriate intervention an improvement with respect to all three parameters can be observed.
Figure 2:
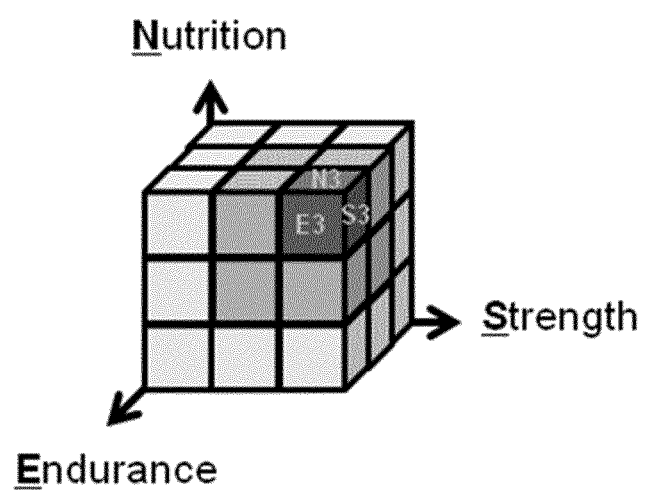

Older people/adults or elderly are defined to be human beings that are older than 60. In particular, they can have an age above 65, 70, 75, 80, 85, or 90. They can also have an age between 60 and 90 years, 65 and 90, 70 and 90 years, 75 and 90 years, 80 and 90 years, 85 and 90 years, or between 60 and 85 years, 60 and 80 years, 60 and 75 years, 60 and 70 years, 60 and 65 years. Any combination of the upper and lower limits regarding age as defined above is also considered to be disclosed here.

About is defined to define a range in relation to a particular numerical value. The range can be +/−10%, +/−7.5%, +/−5%, +/−2.5%, or +/−1% in relation to the particular numerical value.

Scoring is a method by which a numerical value obtained by a test method performed by a subject is related/transformed to a further piece of information usually a further number to give standardized information on the performance of said subject in said test. For example, the walking speed of a subject might be 2 m/sec. For a speed of 0-1 m/sec the score has been defined to be 1. For a speed of above 1 m/sec to 2.5 m/s the score has been determined to be 2 and for above 2.5 m/sec the score has been defined to be 3. Thus, the walking speed of the subject can be scored to be 2.

A Physical Activity Readiness Questionnaire (PAR-Q) is a 1-page form to see if you should check with your physician before becoming much more physically active (see http://www.csep.ca/cmfiles/publications/parq/par-q.pdf retrieved on Jan. 4, 2013).

The functional aerobic capacity can be broadly described as a combination of cardiorespiratory fitness and functional ability. The former (cardiorespiratory fitness) refers to the ability of the circulatory and respiratory systems to provide oxygen to skeletal muscle and is characterized classically by the maximal oxygen consumption (VO2max), which can be measured directly during a maximal exercise test or indirectly by a submaximal test (heart rate measure). The latter (functional ability) generally refers to the ability of the individual to perform physical tasks (e.g. walk a given distance). These two are often linked as individuals with greater functional ability often have greater levels of habitual activity and therefore cardiorespiratory fitness (DiPietro L, J Gerontol A Biol Sci Med Sci 56(2):13-22, 2001).

One Metabolic Equivalent Task (MET) is the energy expended at rest. Two METs indicates the energy expended is twice that at rest. Three METs is triple the resting energy expenditure, etc. Thus, the METs per hour score is a measure of the intensity of a physical activity.

The ratio of the metabolic rate of the average person while seated and resting, to the metabolic rate of a particular person while performing some task. The symbol MET comes from metabolic equivalents of task. It is commonly used in medicine to express metabolic rates measured during a treadmill test. Two definitions of the MET are essentially equivalent:

1 MET is equivalent to a metabolic rate consuming 3.5 milliliters of oxygen per kilogram of body weight per minute.

1 MET is equivalent to a metabolic rate consuming 1 kilocalorie perkilogram of body weight per hour.

In a treadmill test, actually measuring METs requires that the person being tested wear a mask in order to measure his or her oxygen consumption (and the carbon dioxide exhaled). However, METs are often estimated on the basis of other factors.

METs can be converted to kilocalories consumed per minute: kcal/min=METs×body weight in kilograms÷60.

Adapted from Compendium of Physical Activities. Ainsworth, B E et al. Medicine Science in Sports and Exercise. Vol 25, Pg 713 (1993) and Vol 32, S498 (2000).

To get weekly MET scores, multiply MET value for each activity by hours expended in that activity each time, then add all weekly activities.

DETAILED DESCRIPTION OF THE INVENTION

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/v) values.

Basic Concept of Invention

The present invention relates a new integrated, holistic approach to empower older adults to enhance their quality of life and independence through a personalized lifestyle and nutrition program. The invention relates to tools for achieving these goals. In particular, the aim of the invention is to propose a battery of test evaluating the physical condition (and the nutritional state) of older subjects to be able to propose personalized recommendations for a personalized training program (including also some nutritional recommendations)

In a first aspect, a method is provided that allows to assess the health status of a person, in particular an older adult, by a variety of tests for evaluating individual aspects of the health status. In a second aspect, the results of those evaluations are used to provide to those persons tested personalized advice on improving their health status.

The evaluation of the first aspect takes place in three dimensions or, in other words, by using three parameters. These dimensions are nutrition, physical endurance, and physical strength. The values of these parameters are determined for each person individually. The determined values allow to score the persons into certain classes. For each group a predetermined advice for a nutritional and training program can be provided in the second aspect. It is important that based on the recommendations regarding a training program that aims to improve the strength or endurance of a person the nutritional needs need to be adapted. Furthermore, the choice of the nutritional program opens new potentials for adapted training programs. Thus, there is an interplay of the three dimensions respectively parameters. This is the first time that the interrelation between these three dimensions and parameters is considered when addressing the needs of the elderly with respect to their health status. Moreover, the recommendations are provided on a personalized level tailored to the needs of the individual person.

Overview Over the Methods of the Invention

As mentioned above the beginning of the method resides in the assessment of the relevant parameters (endurance, strength, nutrition).

Figure 4:
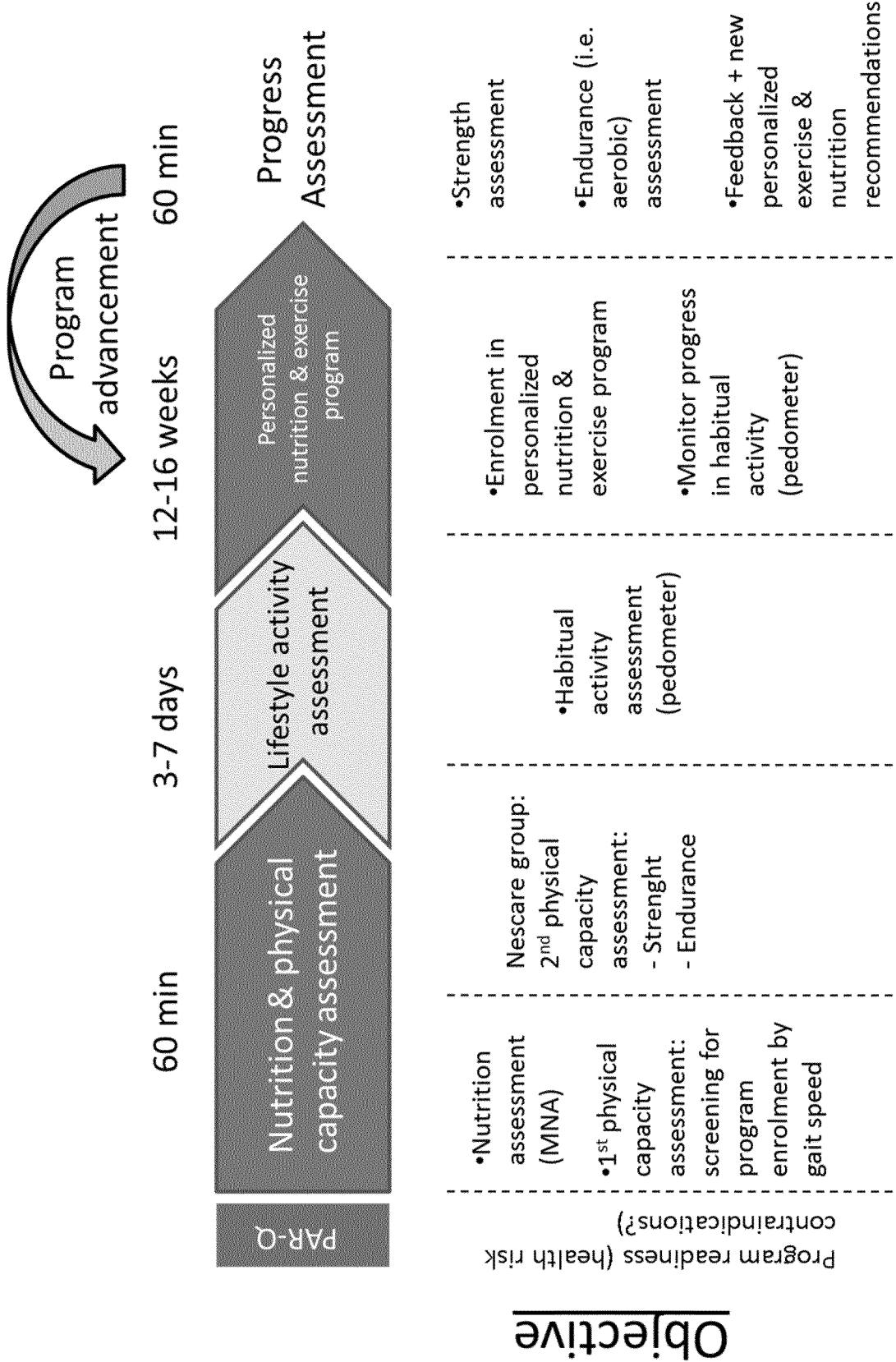
FIG. 4 provides an example of an overview over the combined methods of the invention on a time axis.

Prior to this assessment the person might be individually tested for their readiness for the assessment method of the invention (Pre-assessment, program readiness e.g. with the PAR-Q questionnaire, see FIG. 4). Depending on the result of the PAR-Q, subjects will therefore do a walk test (e.g. the 4 m walk test) evaluating their gait speed related to their ability to follow the program. This is the $1^{st}$ physical capacity assessment. For example, it would not be useful to subject persons to the claimed method if they have a health status that is already optimal and does not need any further improvement or when their health status is so deteriorated that they cannot be subjected to the physical assessment tests. In the latter case, the health risk contraindications would forbid to apply the assessment methods of the inventions to the relevant persons.

Thus, the invention aims to assist people who are at risk of sliding into functional decline. This population would be healthy enough to participate but also have the best chance for benefit. Therefore, the whole invention aims to fight against further functional decline.

Thus, after the PAR-Q questionnaire, the first physical capacity assessment is the measurement of the gait speed, both of them being performed in a short period of between 5 and 20 min or 10-15 min.

The $2^{nd}$ physical capacity assessment is the main assessment of the invention measures comprises a strength assessment, endurance assessment, and nutrition assessment. This $2^{nd}$ series of tests will be performed within 20 to 90 min, 25 to 70 min, 30 to 60 min, 40 to 60 min or about 50 min. The nature of the strength assessment, endurance assessment, and nutrition assessment will be discussed under separated headings.

After the $2^{nd}$ physical capacity evaluation, a subsequent test of habitual activity can be performed. Habitual activity tests analyze how often or/and how much a person engages in physical activity like walking A well-known form for measuring habitual activity is a pedometer. The habitual activity might be tested for a period of 1 to 10 days, 2-8 days, 3-7 days, or 5 days or 6 days. In general, a person can make between 1000 and 10000 steps a day which can be measured by a pedometer. A person making between 10,000 and 6000 steps can be considered an active person. A person making less than 6000 steps per day can be considered a less active person. A person making less than 1000 step represents a frail (e.g. old) person.

Based on the results of the main assessment each person enrolls in a personalized nutrition and exercise program. This program will last for 8 to 26, 12-20, or about 16 weeks. Progress and compliance with the program can be optionally controlled by monitoring habitual activity. After this personalized nutrition and exercise program is completed and further main assessment comprising a strength assessment, endurance assessment, and nutrition assessment is performed. In this way progress of the person with regard to the measured parameters can be determined. Based on the report of the progress the personalized nutrition and exercise program can be modified or cancelled. Thus, the method of the invention allows to periodically modify the personalized nutrition and exercise program based on the results of the main assessment to optimize the benefit for the person. An illustration of this process is provided in FIG. 4. Accordingly, in an embodiment the invention relates to an reiterative process wherein based on the results of the main assessment an personalized nutrition and exercise program is chosen and the effects of said program are reassessed after a defined period and based on these reassessment the personalized nutrition and exercise program is modified. The last two steps can be performed at least 2, 3, 4, 5, 6, 7, 8, 9, 10 or more times. Prior to this feedback loop the method can comprise a pre-assessment to decide whether a person is eligible for the main assessment.

First Assessment

The first assessment test is a method that serves to evaluate whether a person is suitable to the subjected to the main assessment method. The first evaluation tests will generally impart less demanding test conditions on the persons to be tested.

The Physical Activity Readiness Questionnaire (PAR-Q) serves to quickly check that the tests and exercises that are proposed are medically safe from a cardiac point of view. Depending on the PAR-Q result, subject will do a walk test (e.g. a 4 m walk test) to do a first evaluation of their physical capacity: they will have to do a walk over a certain distance where the person is asked to walk over said distance with the maximum possible speed. The measured speed of the person over said distance allows to determine whether the person qualifies for the main assessment method. A measured value that is below a predetermined lower limit indicates that the person is not suitable for the main assessment. In those cases, the person is usually to frail and the person should undergo further medical examination, for example, performed by a geriatrician. A measured value that is above a predetermined upper limit indicates that the person is not suitable for the main assessment either. In those cases, the person is usually sufficiently healthy and thus does not need further recommendations regarding its lifestyle. A measured value that is between a predetermined lower limit and a predetermined upper limit indicates that the person is suitable for the main assessment.

In particular, embodiments the walk might be a walk having a length of between 2-6 m, 3-5 m, or 4 m. Preferentially, the walk has a length of 4 m. The lower limit as described above might be a value between 0.4 and 0.8 m/s, 0.5 and 0.7 m/s, or 0.6 m/s. The upper limit as described above might be a value between 1.3 and 1.7 m/s, 1.4 and 1.6 m/s m, or 1.5 m/s. In a preferred embodiment, the lower limit is 0.6 m/s and the upper limit is 1.5 m/s.

Main Assessment

The main assessment method comprises an endurance assessment method, strength assessment method and a nutrition assessment method. The assessment can also consider factors like age, sex, or the results of anamnesis of the person that is subjected to the tests. These factors can affect the scoring of the determined test values.

Endurance Assessment

The endurance assessment method can comprise at least one test for assessing the endurance of a person (e.g. cardiorespiratory fitness) and/or the functional ability of an individual (e.g. ability to perform given activity of daily living task such as walking) The endurance test method can comprise 1, 2, 3, 4, 5, 6, 7, 8, 9, or 10 particular (sub) endurance test methods. For example, one test method might be a walk test or a bicycle ergometer test.

The values obtained from the at least one test for assessing the endurance of a person are scored and can be used to classify the endurance of the person using a predetermined number of classes. The classes are delimited against each other by pre-set limits (cut-off values). Preferentially, the number of classes is 3, 5, 6, 7, 8, 9, or 10. However, the number of classes for each endurance assessment method should be the same. The determined classes for each endurance assessment can be combined by assigning a numerical value to the classes and calculating an average value or combining the numerical values in a weighted manner. The numerical value assigned to each class will be different for each class and be incremental. Each class will indicate a certain endurance of the person. For example, a higher numerical value assigned to a class can indicate a higher endurance of said person. In a particular example, there will be three classes assigned to the values obtained in the endurance assessment tests and the classes will be designated as E1, E2, or E3, wherein E1 indicates that the measured endurance is below a certain lower predetermined limit and E3 indicates that the measured endurance is above a certain higher predetermined limit. E2 indicates that the measured endurance is below a certain higher predetermined limit and is above a certain lower predetermined limit. This scheme of classes can also be defined to contain more than three classes with predetermined limits defining the membership to one class (e.g. E1, E2 E3, E4, E5).

The endurance assessment method can comprise at least one method for determining the endurance by having a person walk for a predetermined time or over a certain distance. During such a test the functional aerobic capacity which is directly related to the ability to do a certain walk distance in a defined time can be determined to yield a certain value. In a preferred endurance assessment method the method comprises only the walk test method.

In a preferred method, the aerobic capacity of a person is determined who has a walk for 4 to 8 min, 5 to 7 min, or 6 min.

In a preferred method, the distance is determined which a person is capable of walking within the set time. In a preferred embodiment, the distance covered by a person is scored differently dependent on the sex of the person.

In a preferred method, the walk test measures the distance covered by a person during a period of 6 minutes.

Strength Assessment

The strength assessment method can comprise at least one test for assessing the strength of a person. The strength assessment method can comprise at least one method for determining the strength of the upper body and/or at least one method for determining the strength of the lower body. The lower body is considered to refer to that part of the body that starts below the shoulder muscles but is mainly comprised of the hip and proximal and distal leg muscles. The upper body is considered to refer to that part of the body that starts with the shoulder muscles and extends distally to the finger tips and includes the upper arm and forearm muscles. A preferred method for determining the strength of the upper body is the determination of the handgrip strength. A preferred method for determining the strength of the lower body is the performance of a sit/stand test. In a sit/stand test it is determined how many times a person is able to stand up from a sitting position before sitting down again within a predetermined time without using his hands.

The predetermined time for the sit/stand test can be between 20 and 40 seconds, 25 and 35 seconds, and 30 seconds.

The hand grip strength can be measured by via a hand held dynamometer (e.g. GRIP-D, T.K. 5401, Takei Scientific Instruments, Tokyo, Japan) wherein the output value is provided in N or kg.

The values obtained from the at least one test for assessing the strength of a person can be used to classify the strength of the person using a predetermined number of classes. In a preferred embodiment, the values obtained by each strength assessment method are grouped into a limited number classes. Preferentially, the number of classes is 3, 5, 6, 7, 8, 9, or 10. However, the number of classes for each strength assessment method should be the same. The determined classes for each strength assessment can be combined by assigning a numerical value to the classes and calculating an average value or combining the numerical values in a weighted manner. Each class will indicate a certain indicated strength of the person. For example, a higher numerical value assigned to a class can indicate a higher strength of said person. In a particular example, there will be three classes assigned to the values obtained in the strength assessment tests and the classes will be designated as S1, S2, or S3, wherein S1 indicates that the measured strength is below a certain lower predetermined limit and S3 indicates that the measured strength is above a certain higher predetermined limit. S2 indicates that the measured strength is below a certain higher predetermined limit and is above a certain lower predetermined limit. This scheme of classes can of course be also defined to contain more than three classes with predetermined limits defining the membership to one class.

Nutrition Assessment

The Mini-Nutritional Assessment (MNA®) is a validated nutrition screening and assessment tool that can identify geriatric patients age 65 and above who are malnourished or at risk of malnutrition. The MNA® was developed nearly 20 years ago and is the most well validated nutrition screening tool for the elderly. Originally comprised of 18 questions, the current MNA® now consists of 6 questions and streamlines the screening process. The current MNA® (see e.g. Skates J J, Anthony P S. Identifying geriatric malnutrition in nursing practice: the Mini Nutritional Assessment (MNA®)-an evidence-based screening tool J Gerontol Nurs 2012; 38(3): 18-27; quiz 28-29 and http://www.mna-elderly.com/default.html retrieved on Jan. 4, 2013) retains the validity and accuracy of the original MNA® in identifying older adults who are malnourished or at risk of malnutrition. The revised MNA Short Form makes the link to intervention easier and quicker and is now the preferred form of the MNA® for clinical use.

Another evaluation of the nutrition status of the subject will be the usual daily intake of protein using the Food Frequency-Protein Intake form.

To determine if the client's protein intake is adequate or inadequate, multiply the client's weight (in kg) by 1.2. A usual intake of 1.2 grams protein/kg/day is considered adequate. Using the subject's MNA® score and evaluation of the adequacy of protein intake, determine the subject's Nutrition Designation based on the following:

| Designation | MNA ® Score | Protein Intake |
| --- | --- | --- |
| N1 | Malnourished | Adequate or inadequate |
| N2 | At risk for PCM with weight loss | Adequate or inadequate |
| N3 | At risk for PCM without weight loss OR | Adequate or inadequate |
|  | Normal nutrition | Inadequate |

Additional Assessments

The main assessment can also comprise the consideration of other parameters like age, sex, weight, height, or the anamnesis of the person that is subjected to the tests.

Recommendations on Exercise Programs

Based on the scores determined in the previous steps an exercise program is selected or recommended for the person. Lower scores are associated with less demanding exercise programs and higher scores result in the selection or recommendation of more demanding exercise programs. If the assessment of endurance or strength comprises more than one assessment method the scores can be combined by determining the average score. For example, if the strength assessment methods comprises determining hand grip strength and sit-to-stand assessment and the score in the first test is 1 and in the second test is 2 the average will be 1.5. Based on the scores the persons can be grouped into classes and thus an exercise or a set of exercises can be recommended.

More demanding exercises are exercises which take longer or/and done with a higher intensity level or/and are repeated more often in a predetermined fixed time period than less demanding exercises. It is also an option to perform a "challenge" which is an exercise performed within a shorter period of time but with higher intensity compared to the exercises of the usual exercise programs.

For example, if the strength classification system comprises three classes the recommended exercise unit can comprise for the class (named e.g. S1) that is associated with the least demanding at least one exercise unit which can be between 10 and 20 min or 15 min. The unit is to be performed 3 times per week.

In the class (named e.g. S2) associated with the more demanding exercise program the at least one exercise unit can be between 20 and 30 min or 20 min. The unit is to be performed 3 times per week.

In the class (named e.g. S3) associated with the most demanding exercise program the at least one exercise unit can be between 30 and 40 min or 35 min. The unit is to be performed 3 times per week.

If more than one test is used to classify the person into the system the scores might differ. These might be indicative of a physical imbalance between different tested areas of the body. In those cases the exercise unity might be adapted to train the area of the body that appears to be in a weaker physical condition.

In a preferred embodiment, the endurance classification system comprises three classes. For a class (named e.g. E1) can be associated with the least demanding exercise program. The exercise program might comprise at least one exercise unit. The unit can be between 10 and 20 min or 15 min. The unit is to be performed 3 times per week.

In the class (named e.g. E2) associated with the more demanding exercise program the at least one exercise unit can be between 20 and 30 min or 20 min. The unit is to be performed 3 times per week.

In the class (named e.g. E3) associated with the most demanding exercise program the at least one exercise unit can be between 30 and 40 min or 35 min. The unit is to be performed 3 times per week.

Recommendations on Nutrition

Based on the classes obtained for the nutritional status certain nutritional recommendations can be provided to the persons. The nutritional recommendations aim at the maintenance or improvement of the physical parameters of the person that are important for the physical mobility of a person. In particular, these physical parameters are bone mass, muscle mass, muscle strength, integrity of joints. Thus, the nutrition should contain bioactive nutrients both in the form of a complete nutrition or in the form of supplemental nutritional agents. The bioactive nutrients of the invention have an effect on the maintenance of bone mass, muscle mass, muscle strength, integrity of joints, i.e. protect joints and/or improve the comfort of the person. Examples for bioactive nutrients are an increased protein supplementation, particular protein supplements (like whey protein), calcium, vitamin D etc.

Computer Implemented Methods and System

Any of the above methods insofar as they relate to receiving, processing and outputting of data can be implemented as software programs and executed on computers.

The invention is directed to a computer implemented method for determining the physical status of a subject comprising: providing a database comprising a classification system for the parameters nutrition, physical endurance, and physical strength of said subject wherein the classification system associates numerically determined values of said parameter with scores for said values, and said system also associates said scores with classes and said system associates said classes with an indication of particular physical status, inputting values for said parameters which have been determined by functional physical tests in said subject, using said values to score those values for each parameter according to the database, using the obtained scores to classify the subject into classes with respect to each of said parameters according to said database, using said determined classes for each parameter to determine an indication of a physical status of said subject, and outputting said indication of the physical status for said subject.

The subject can be an older subject, preferentially a human subject being older than 65 years. The parameter endurance can be assessed by at least one endurance test. The endurance test can be selected from the group consisting of measuring the distance achieved in a walk test (e.g. 6 minutes walk test).

The parameter strength can be assessed at least by measuring the strength with a hand grip test or a sit to stand test.

The parameter nutrition can be assessed by at least one nutrition test. The nutrition test can be the MNA.

The computer implemented method can comprise additional steps. The database might then also comprise recommendations for the subject with respect to nutrition, physical endurance, and physical strength based on the determined classes. The method might then also contain the step of associating the determined classes with the specific recommendations and outputting those recommendations.

The exercise program can be different for each determined class but also according to individual preferences.

In a further embodiment a system for determining the physical status of a subject is disclosed, said system comprising a computer: said computer stores a data base comprising a classification system for the parameters nutrition, physical endurance, and physical strength of a subject; said computer stores a software program having instructions causing the computer to receive and store the values of said parameters in said subject; to score values of said parameters for said subject; to use the obtained scores to classify the subject into classes with respect to each of said parameters; calculate a value for the physical status of said subject based on said classes.

Furthermore, a system for facilitating the improvement of a physical status of a subject is disclosed, said system comprising a computer said computer stores a data based comprising a classification system for the parameters nutrition, physical endurance, and physical strength of a subject; said computer stores a data base comprising a classification system for the parameters nutrition, physical endurance, and physical strength of a subject; said computer stores a software program having instructions causing the computer to receive and store the values of said parameters in said subject; to score values of said parameters for said subject; to use the obtained scores to classify the subject into classes with respect to each of said parameters; calculate a value for the physical status of said subject based on said classes, associating said value of the physical status with particular recommendation for said subject, outputting recommendations for the subject with respect to nutrition, physical endurance, and physical strength based on the determined classes.

In a further embodiment a method for personalizing elderly care comprising the steps of: creating a database relating to physical functional tests and their validity to identifying the overall physical status of select elderly patient populations; storing the database on a computer; executing a computer program causing the computer to determine viable functional test results relating to strength and endurance in specific elderly patient populations, the test results including end points relating to nutrition, strength and endurance; and executing a program that uses the end points to generate guidelines based on nutrition, strength and endurance test results that can be used to personalize a nutrition and exercise program for a member of the specific elderly population.

At least two or three different programs are used by the computer.

The computer program can be executed by the computer to personalize the nutrition and exercise program for the member. The computer program can also contain a step relating the physical status to recommendations for the member and outputting those recommendations. During the program the member can be monitored to determine nutrition, strength and endurance. Depending on the results of the monitoring the nutrition and exercise program can be modified. The exercise programs can be endurance and strength exercise programs adapted to the particular needs of the member.

EXAMPLES

Example 1: Endurance Classification

The endurance is one parameter of the three parameters to be tested and can be assessed in a 3-class system (see FIG. 1).

A 6 minute walk is performed and the performance of the test subject is scored and classified (E1-E3) according to the following scheme:

| Distance (m) | | METS* | Designation |
| Male | Female | | |
|---|---|---|---|
| <420 | <380 | <3 | E1 |
| 420-520 | 380-475 | 3-4 | E2 |
| >520 | >475 | >4 | E3 |

*Rough equivalence based on average speed and corresponding MET can be individually estimated from test results and used as guideline for recommended exercise.

Based on the determined class particular recommendations are provided with respect to an exercise program:

| Program | Recommended exercise** | Challenge | Goals for improvement (12-16 wks) |
|---|---|---|---|
| E1 | 15 min/d @ >3METs | ≥5 min/d @ ≥5 METs | Basal step counts + 50% |
| E2 | 25 min/d @ >3METs | ≥8 min/d @ ≥5 METs | Basal step counts + 40% |
| E3 | 35 min/d @ >3METs | ≥11.5 min/d @ ≥5 METs | Basal step counts + 30% |

As indicate above progress in relation to the set goals can be tightly monitored.

Example 2: Strength Classification

Figure 3:
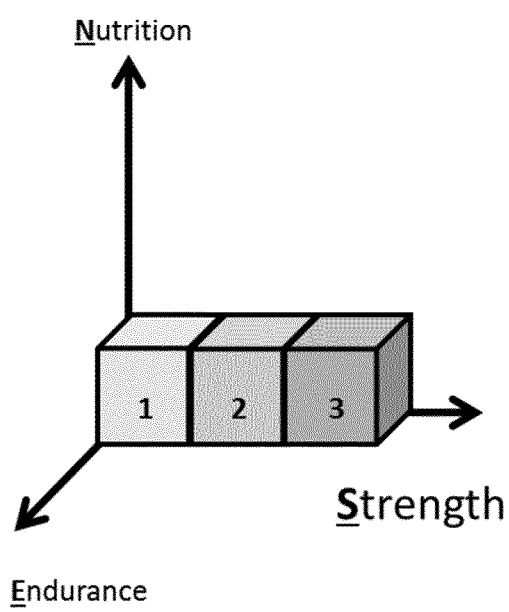
FIG. 3 schematically shows how a person within the three-parameter scheme can be assessed with respect to the parameter strength.

The strength is one parameter of the three parameters to be tested and can be assessed in a 3-class system (see FIG. 3).

The strength test in this example comprises two subtests (hand grip strength and sit-to-stand test).

The hand grip strength and sit-to-stand test are performed and the performance of the test subject is scored according to the following schemes:

Hand grip strength:

| Strength (kg) | | Score* |
| Male | Female | |
|---|---|---|
| <30 | <17 | 1 |
| 30-42 | 17-25 | 2 |
| >42 | >25 | 3 |

Sit-to-stand within 30 seconds.

| Repetitions | | Score* |
| Male | Female | |
|---|---|---|
| ≤10 | ≤9 | 1 |
| 11-14 | 10-13 | 2 |
| ≥15 | ≥14 | 3 |

The average of the scores in the sub-tests is formed. The average score allows to group the performance into classes (S1-S3) and provide specific recommendations regarding the exercises:

| Program (score) | Recommended exercise | Challenge* | Goals for improvement (12-16 wks) |
|---|---|---|---|
| S1 (≤1.5) | 15 min/d, 3X/week strength exercises | Final repetition RPE = 6-7 | Sit-to-stand + 2 Hand grip + 3 kg |
| S2 (2 ≤ 2.5) | 25 min/d, 3X/week strength exercises | Final repetition RPE = 7-8 | Sit-to-stand + 3 Hand grip + 3 kg |
| S3 (3) | 35 min/d, 3X/week strength exercises | Final repetition RPE = 8-9 | Sit-to-stand + 4 Hand grip + 3 kg |

*Optionally, if discrepancies in score exist between upper/lower body, exercise recommendations will target weakness to correct "imbalance". For example, if scores are 1 and 2 for hand grip and sit-to-stand, respectively, then ~65% and ~35% of exercise can target upper vs. lower body, respectively.

The invention claimed is:

1. A method for improving a physical status of a subject older than 65 years, the method comprising:
   (a) performing a computer-implemented process comprising:
      (a0) determining whether the subject is suitable for being subjected to the method by measuring a maximum speed of the subject walking over a first predetermined distance and comparing the maximum speed to a predetermined lower limit and a predetermined upper limit, the maximum speed being lower than the predetermined lower limit indicates that the subject is frail such that the subject is not further subjected to the method, the maximum speed being above the predetermined upper limit indicates that the subject is healthy such that the subject is not further subjected to the method, and the maximum speed being between the predetermined lower limit and the predetermined upper limit indicates that the subject is suitable for the remainder of the method, wherein the predetermined lower limit is between 0.4 and 0.8 m/s and the predetermined upper limit is between 1.3 and 1.7 m/s;
      (a1) providing a classification system for parameters comprising nutrition, physical endurance, and physical strength of the subject;
      (a2) assessing and scoring values of the parameters in the subject to obtain scores, wherein the assessing of the values for the physical strength of the subject comprises determining an upper body strength of the subject by measuring a handgrip strength of the subject and determining a lower body strength of the subject by a sit/stand test, and wherein the assessing of the values for the physical endurance of the subject comprises determining functional aerobic capacity of the subject after having the subject walk for a predetermined time and/or over a second predetermined distance;
      (a3) using the scores to classify the subject into classes with respect to each of the parameters, wherein the classes for the physical strength comprise at least a first class for the scores below a first pre-set limit, a second class for the scores above the first pre-set limit and below a second pre-set limit, and a third class for the scores above the second pre-set limit; and
      (a4) providing recommendations for the subject based on the classes, the recommendations are for the nutrition, the physical endurance, and the physical strength of the subject, and the recommendations for the first class, the recommendations for the second class, and the recommendations for the third class are different relative to each other; and
   (b) administering bioactive nutrients to the subject according to the recommendations.

2. The method according to claim 1, wherein the nutrition of the subject is assessed by Mini-Nutritional Assessment and/or evaluation of daily protein intake.

3. The method according to claim 1, wherein the subject is classified within 30 minutes of the assessing and scoring.

4. The method according to claim 1, wherein steps of the computer-implemented process are repeated in defined intervals.

5. The method according to claim 1, wherein the bioactive nutrients administered to the subject improve the physical endurance and the physical strength of the subject.

6. The method according to claim 1, wherein the recommendations identify a particular exercise program based on the class for the physical endurance of the subject, wherein the exercise program is different for each determined class.

7. The method according to claim 1, wherein the recommendations identify a particular exercise program based on the class for the physical strength of the subject, wherein the exercise program is different for each of the first, second and third classes relative to each other.

8. The method according to claim 1, wherein the assessing of the values for the endurance further comprises the subject performing a bicycle ergometer test.

9. The method according to claim 1 comprising measuring habitual activity of the subject, using a pedometer, to monitor progress and compliance by the subject for an exercise program identified by the recommendations.

10. The method according to claim 1, wherein the recommendations are adapted to maintain and/or improve the parameters of the subject.

11. The method according to claim 10, wherein the parameters are selected from the group consisting of bone mass, muscle mass, muscle strength, integrity of joints, and combinations thereof.

12. The method according to claim 10, wherein the bioactive nutrients are administered in effective amounts for maintenance and/or improvement of the parameters of the subject.

13. The method according to claim 1, wherein the functional aerobic capacity of the subject is determined by measuring a ratio of a first metabolic rate of the subject while performing the walk to a second metabolic rate of the subject while seated and resting.

* * * * *